(12) United States Patent
van Wezel et al.

(10) Patent No.: US 7,022,526 B2
(45) Date of Patent: Apr. 4, 2006

(54) REDUCING BRANCHING AND ENHANCING FRAGMENTATION IN CULTURING FILAMENTOUS MICROORGANISMS

(75) Inventors: Gilles Philippus van Wezel, Leiden (NL); Barend Kraal, Leiden (NL); Rudolf Gijsbertus M. Luiten, Leiden (NL)

(73) Assignee: Rijksuniversiteit te Leiden, Leiden (NL)

( * ) Notice: Subject to any disclaimer, the term of this patent is extended or adjusted under 35 U.S.C. 154(b) by 479 days.

(21) Appl. No.: 09/749,185

(22) Filed: Dec. 26, 2000

(65) Prior Publication Data

US 2002/0086412 A1 Jul. 4, 2002

Related U.S. Application Data

(63) Continuation of application No. PCT/NL99/00395, filed on Jun. 25, 1999.

(30) Foreign Application Priority Data

Jun. 26, 1998 (EP) .............................................. 98202148

(51) Int. Cl.
| | |
|---|---|
| C12P 21/06 | (2006.01) |
| C12N 9/00 | (2006.01) |
| C12N 1/20 | (2006.01) |
| C07H 21/04 | (2006.01) |

(52) U.S. Cl. .............................. 435/484; 435/6; 435/41; 435/69.1; 435/183; 435/252.3; 435/254.1; 435/325; 536/23.2; 536/23.4; 536/23.7; 536/23.74

(58) Field of Classification Search ..................... 435/4, 435/6, 69.1, 252.3, 320.1, 254.1, 254.11, 435/252.55, 471, 183, 41, 42.67, 71.3; 536/23.4, 536/23.7, 23.74

See application file for complete search history.

(56) References Cited

PUBLICATIONS

Kwak et al., Differential Regulation of ftsZ Transcription during Septation of *Streptomyces griseus*, Journal of Bacteriology, Sep. 2001, pp. 5092–5101, vol. 183, No. 17.

Kawamoto, Shinichi, et al., "Cloning and Characterization of a Gene Involved in Regulation of Sporulation and Cell Division of *Streptomyces griseus*," Actinomycetol., vol. 9, No. 2, 1995, pp. 136–151.

Kawamoto, Shinichi, et al., "Expression Analysis of the ssgA Gene Product, Associated with Sporulation and Cell Division in *Streptomyces griseus*," Microbiology, vol. 143, 1997, pp. 1077–1086.

*Primary Examiner*—Manjunath N. Rao
(74) *Attorney, Agent, or Firm*—TraskBritt

(57) ABSTRACT

The invention relates to the field of microorganisms and to the culturing of microorganisms. Means and methods are described for enhancing the culturing properties of filamentous microorganisms, particularly filamentous fungi. According to the invention, the means and methods generally comprise reducing the branching and/or enhancing the fragmentation of the microorganisms, so that their liquid culturing properties are improved. In one embodiment, this is achieved by providing the microorganisms with activity capable of enhancing fragmentation and/or reducing branching such as the activity which in, for example, *Streptomyces griseus* is encoded by ssgA.

13 Claims, 15 Drawing Sheets

A

B

Figure 1:
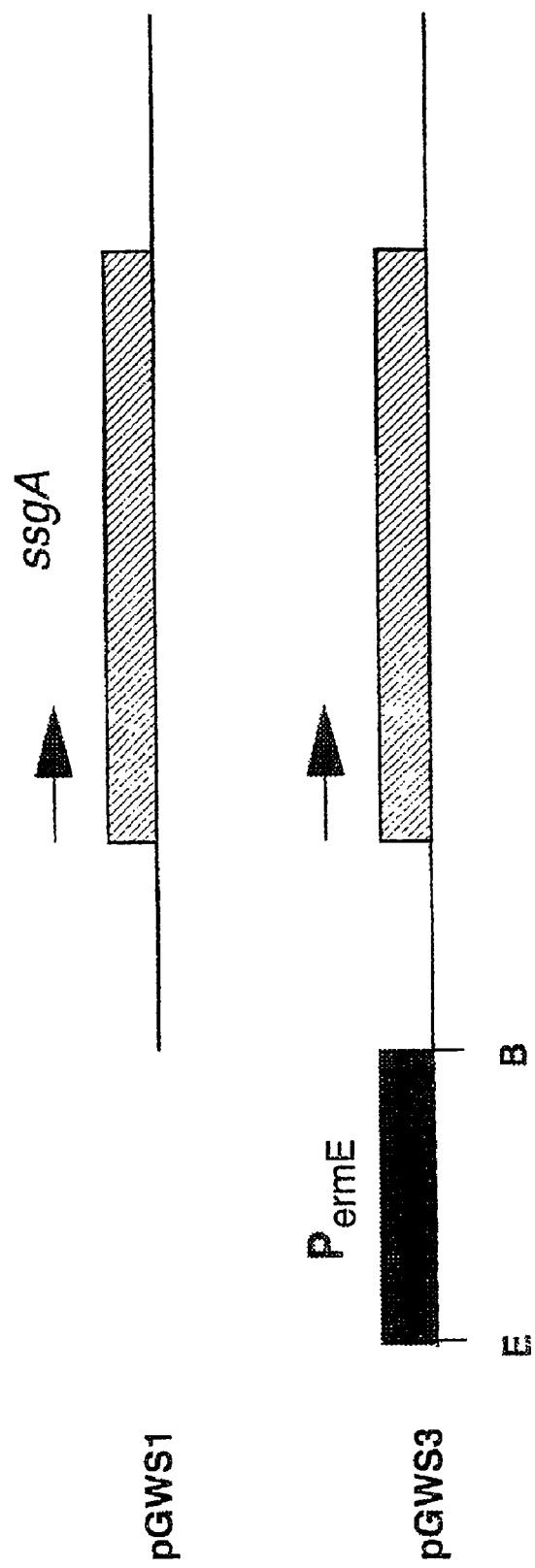

SEQUENCE LISTING (1) GENERAL INFORMATION:

(i) APPLICANT:
        (A) NAME: Rijksuniversiteit Leiden
        (B) STREET: Stationsweg 46
        (C) CITY: Leiden
        (D) STATE: Zuid-Holland
        (E) COUNTRY: the Netherlands
        (F) POSTAL CODE (ZIP): 2312 AV (A) NAME: Nederlandse Organisatie voor Wetenschappelijk Onderzoek/Chemische Wetenschappen/STW
        (B) STREET: Laan van Nieuw Oost Indie 131
        (C) CITY: The Hague
        (D) STATE: Zuid-Holland
        (E) COUNTRY: the Netherlands
        (F) POSTAL CODE (ZIP): 2593 BM (ii) TITLE OF INVENTION: Reducing branching and enhancing fragmentation in culturing filamentous microorganisms.

(iii) NUMBER OF SEQUENCES: 13

(iv) COMPUTER READABLE FORM:
        (A) MEDIUM TYPE: Floppy disk
        (B) COMPUTER: IBM PC compatible
        (C) OPERATING SYSTEM: PC-DOS/MS-DOS
        (D) SOFTWARE: PatentIn Release #1.0, Version #1.30 (EPO)

(v) CURRENT APPLICATION DATA:
        PRIORITY APPLICATION NUMBER : EP 98202148.7

(2) INFORMATION FOR SEQ ID NO: 1:

(i) SEQUENCE CHARACTERISTICS:
        (A) LENGTH: 438 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) Original Source: (A) Organism: Streptomyces griseus
                          (B) Strain: ATTC 23345

(ix) FEATURE:
        (A) NAME/KEY: CDS
        (B) LOCATION: 1..408
        (D) OTHER INFORMATION: /product= "SsgA"
            /gene= "ssgA"

(xi) SEQUENCE DESCRIPTION: SEQ ID NO: 1:

ATGCGCGAGT CGGTTCAAGC AGAGGTCATG ATGAGCTTCC TCGTCTCCGA GGAGCTCTCG 60

TTCCGTATTC CGGTGGAGCT CCGATACGAG GTCGGCGATC CGTATGCCAT CCGGATGACG 120

Fig. 5

```
TTCCACCTTC CCGGCGATGC CCCTGTGACC TGGGCGTTCG GCCGCGAGCT GCTGCTGGAC
180

GGGCTCAACA GCCCGAGCGG CGACGGCGAT GTGCACATCG GCCCGACCGA GCCCGAGGGC
240

CTCGGAGATG TCCACATCCG GCTCCAGGTC GGCGCGGACC GTGCGCTGTT CCGGGCGGGG
300

ACGGCACCGC TGGTGGCGTT CCTCGACCGG ACGGACAAGC TCGTGCCGCT CGGCCAGGAG
360

CACACGCTGG GTGACTTCGA CGGCAACCTG GAGGACGCAC TGGGCCGCAT CCTCGCCGAG
420

GAGCAGAACG CCGGCTGA
438

(2) INFORMATION FOR SEQ ID NO: 2:

(i) SEQUENCE CHARACTERISTICS:
        (A) LENGTH: 408 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (A) ORGANISM: Streptomyces griseus
        (B) STRAIN: ATTC 23345

(ix) FEATURE:
        (A) NAME/KEY: CDS
        (B) LOCATION: 1..408
        (D) OTHER INFORMATION: /product= "SsgA"
                               /gene= "ssgA"

(xi) SEQUENCE DESCRIPTION: SEQ ID NO: 2:

ATG AGC TTC CTC GTC TCC GAG GAG CTC TCG TTC CGT ATT CCG GTG GAG
48
Met Ser Phe Leu Val Ser Glu Glu Leu Ser Phe Arg Ile Pro Val Glu
 1               5                  10                  15

CTC CGA TAC GAG GTC GGC GAT CCG TAT GCC ATC CGG ATG ACG TTC CAC
96
Leu Arg Tyr Glu Val Gly Asp Pro Tyr Ala Ile Arg Met Thr Phe His
             20                  25                  30

CTT CCC GGC GAT GCC CCT GTG ACC TGG GCG TTC GGC CGC GAG CTG CTG
144
Leu Pro Gly Asp Ala Pro Val Thr Trp Ala Phe Gly Arg Glu Leu Leu
         35                  40                  45

CTG GAC GGG CTC AAC AGC CCG AGC GGC GAC GGC GAT GTG CAC ATC GGC
192
Leu Asp Gly Leu Asn Ser Pro Ser Gly Asp Gly Asp Val His Ile Gly
     50                  55                  60

CCG ACC GAG CCC GAG GGC CTC GGA GAT GTC CAC ATC CGG CTC CAG GTC
```

Fig. 5 cont.

```
                                                240
Pro Thr Glu Pro Glu Gly Leu Gly Asp Val His Ile Arg Leu Gln Val
65                   70                  75                  80

GGC GCG GAC CGT GCG CTG TTC CGG GCG GGG ACG GCA CCG CTG GTG GCG
288
Gly Ala Asp Arg Ala Leu Phe Arg Ala Gly Thr Ala Pro Leu Val Ala
                85                  90                  95

TTC CTC GAC CGG ACG GAC AAG CTC GTG CCG CTC GGC CAG GAG CAC ACG
336
Phe Leu Asp Arg Thr Asp Lys Leu Val Pro Leu Gly Gln Glu His Thr
                100                 105                 110

CTG GGT GAC TTC GAC GGC AAC CTG GAG GAC GCA CTG GGC CGC ATC CTC
384
Leu Gly Asp Phe Asp Gly Asn Leu Glu Asp Ala Leu Gly Arg Ile Leu
            115                 120                 125

GCC GAG GAG CAG AAC GCC GGC TG
408
Ala Glu Glu Gln Asn Ala Gly
130                 135
```

(2) INFORMATION FOR SEQ ID NO: 3:

(i) SEQUENCE CHARACTERISTICS:
        (A) LENGTH: 135 amino acids
        (B) TYPE: amino acid
        (D) TOPOLOGY: linear (ii) MOLECULE TYPE: protein (xi) SEQUENCE DESCRIPTION: SEQ ID NO: 3:

```
Met Ser Phe Leu Val Ser Glu Glu Leu Ser Phe Arg Ile Pro Val Glu
1               5                   10                  15

Leu Arg Tyr Glu Val Gly Asp Pro Tyr Ala Ile Arg Met Thr Phe His
            20                  25                  30

Leu Pro Gly Asp Ala Pro Val Thr Trp Ala Phe Gly Arg Glu Leu Leu
            35                  40                  45

Leu Asp Gly Leu Asn Ser Pro Ser Gly Asp Gly Asp Val His Ile Gly
        50                  55                  60

Pro Thr Glu Pro Glu Gly Leu Gly Asp Val His Ile Arg Leu Gln Val
65                  70                  75                  80

Gly Ala Asp Arg Ala Leu Phe Arg Ala Gly Thr Ala Pro Leu Val Ala
                85                  90                  95

Phe Leu Asp Arg Thr Asp Lys Leu Val Pro Leu Gly Gln Glu His Thr
                100                 105                 110

Leu Gly Asp Phe Asp Gly Asn Leu Glu Asp Ala Leu Gly Arg Ile Leu
            115                 120                 125

Ala Glu Glu Gln Asn Ala Gly
130                 135
```

(2) INFORMATION FOR SEQ ID NO: 4:

Fig. 5 cont.

(i) SEQUENCE CHARACTERISTICS:
    (A) LENGTH: 408 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (vi) ORIGINAL SOURCE:
    (A) ORGANISM: Streptomyces albus G
    (B) STRAIN: ATCC 3004

(ix) FEATURE:
    (A) NAME/KEY: CDS
    (B) LOCATION: 1..408
    (D) OTHER INFORMATION: /product= "SsgA"
                           /gene= "ssgA"

(xi) SEQUENCE DESCRIPTION: SEQ ID NO: 4:

ATG AGC TTC CTC GTC TCC GAG GAG CTC GCC TTC CGC ATC CCG GTG GAG
48
Met Ser Phe Leu Val Ser Glu Glu Leu Ala Phe Arg Ile Pro Val Glu
 1               5                  10                  15

CTG CGG TAC GAG ACC GTC GAT CCG TAC GCG GTG CGG CTG ACG TTC CAC
96
Leu Arg Tyr Glu Thr Val Asp Pro Tyr Ala Val Arg Leu Thr Phe His
            20                  25                  30

CTC CCC GGA GAC GCC CCG GTC ACC TGG GTC TTC GGG CGT GAA CTG CTG
144
Leu Pro Gly Asp Ala Pro Val Thr Trp Val Phe Gly Arg Glu Leu Leu
        35                  40                  45

GTC GAG GGA GTC CTG GAC GCC GCG GGC GAC GGC GAC GTC CGG GTC TGC
192
Val Glu Gly Val Leu Asp Ala Ala Gly Asp Gly Asp Val Arg Val Cys
    50                  55                  60

CCG GTG GGG CAG ACG GCC ACC AGG GAG GTG CAC ATC ACC CTC CAG GTC
240
Pro Val Gly Gln Thr Ala Thr Arg Glu Val His Ile Thr Leu Gln Val
65                  70                  75                  80

GGC TCC GAG CAG GCG CTC TTC CGC GTC GGC AAG GCG CCG CTG CTC GCC
288
Gly Ser Glu Gln Ala Leu Phe Arg Val Gly Lys Ala Pro Leu Leu Ala
            85                  90                  95

TTC CTC GAC CGC ACC GAC CAG GGC TTG TCG CTC GGC AGC GAG CGG GCA
336
Phe Leu Asp Arg Thr Asp Gln Gly Leu Ser Leu Gly Ser Glu Arg Ala
            100                 105                 110

CAC GCC GAC TTC GAC AGC CAC CTC GAC GAC GCT CTG AAC CGC AGC CTC
384
His Ala Asp Phe Asp Ser His Leu Asp Asp Ala Leu Asn Arg Ser Leu
        115                 120                 125

GCC GAG GAG CAG AGC GCC GGC TG
408
Ala Glu Glu Gln Ser Ala Gly

Fig. 5 cont.

(2) INFORMATION FOR SEQ ID NO: 5:

(i) SEQUENCE CHARACTERISTICS:
        (A) LENGTH: 135 amino acids
        (B) TYPE: amino acid
        (D) TOPOLOGY: linear (ii) MOLECULE TYPE: protein (xi) SEQUENCE DESCRIPTION: SEQ ID NO: 5:

```
Met Ser Phe Leu Val Ser Glu Glu Leu Ala Phe Arg Ile Pro Val Glu
 1               5                  10                  15

Leu Arg Tyr Glu Thr Val Asp Pro Tyr Ala Val Arg Leu Thr Phe His
            20                  25                  30

Leu Pro Gly Asp Ala Pro Val Thr Trp Val Phe Gly Arg Glu Leu Leu
        35                  40                  45

Val Glu Gly Val Leu Asp Ala Ala Gly Asp Gly Asp Val Arg Val Cys
    50                  55                  60

Pro Val Gly Gln Thr Ala Thr Arg Glu Val His Ile Thr Leu Gln Val
65                  70                  75                  80

Gly Ser Glu Gln Ala Leu Phe Arg Val Gly Lys Ala Pro Leu Leu Ala
                85                  90                  95

Phe Leu Asp Arg Thr Asp Gln Gly Leu Ser Leu Gly Ser Glu Arg Ala
            100                 105                 110

His Ala Asp Phe Asp Ser His Leu Asp Asp Ala Leu Asn Arg Ser Leu
        115                 120                 125

Ala Glu Glu Gln Ser Ala Gly
    130                 135
```

(2) INFORMATION FOR SEQ ID NO: 6:

(i) SEQUENCE CHARACTERISTICS:
        (A) LENGTH: 408 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (A) ORGANISM: Streptomyces goldiniensis
        (B) STRAIN: ATCC 21386

(ix) FEATURE:
        (A) NAME/KEY: CDS
        (B) LOCATION: 1..408
        (D) OTHER INFORMATION: /product= "SsgA"
            /gene= "ssgA"

(xi) SEQUENCE DESCRIPTION: SEQ ID NO: 6:

Fig. 5 cont.

```
ATG AGC TTC CTC GTC TCG GAA GAA CTC TCC TTC CGT ATT CCG GTG GAG
48
Met Ser Phe Leu Val Ser Glu Glu Leu Ser Phe Arg Ile Pro Val Glu
 1               5                  10                 15

CTG CGT TAC GAG ACC TGT GAT CCC TAC GCC GTG CGG CTG ACC TTT CAT
96
Leu Arg Tyr Glu Thr Cys Asp Pro Tyr Ala Val Arg Leu Thr Phe His
            20                  25                  30

CTG CCC GGA GAT GCC CCG GTG ACC TGG GCG TTC GGG CGG GAG TTG CTC
144
Leu Pro Gly Asp Ala Pro Val Thr Trp Ala Phe Gly Arg Glu Leu Leu
        35                  40                  45

ATC GAC GGA GGT CCG CGG CCG TGC GGG GAC GGG GAC GTC CAC ATC GCG
192
Ile Asp Gly Gly Pro Arg Pro Cys Gly Asp Gly Asp Val His Ile Ala
    50                  55                  60

CCC GCC GAC CCG GAG ACG TTC GGC GAG GTC CTG ATC CGC CTG CAG GTG
240
Pro Ala Asp Pro Glu Thr Phe Gly Glu Val Leu Ile Arg Leu Gln Val
65                  70                  75                  80

GGG AGC GAC CAG GCG ATG TTC CGG GTC GGC ACG GCG CCG CTG GTG GCC
288
Gly Ser Asp Gln Ala Met Phe Arg Val Gly Thr Ala Pro Leu Val Ala
                85                  90                  95

TTC CTG GAC CGC ACG GAC AAG ATC GTG CCG CTG GGG CAG GAG CGT TCC
336
Phe Leu Asp Arg Thr Asp Lys Ile Val Pro Leu Gly Gln Glu Arg Ser
            100                 105                 110

CTC GCC GAC TTC GAC GCC CTG CTC GAC GAG GCG CTG GAC CGC ATC CTG
384
Leu Ala Asp Phe Asp Ala Leu Leu Asp Glu Ala Leu Asp Arg Ile Leu
        115                 120                 125

GCC GAG GAG CAG AAC GCC GGC TG
408
Ala Glu Glu Gln Asn Ala Gly
        130                 135

(2) INFORMATION FOR SEQ ID NO: 7:

(i) SEQUENCE CHARACTERISTICS:
            (A) LENGTH: 135 amino acids
            (B) TYPE: amino acid
            (D) TOPOLOGY: linear (ii) MOLECULE TYPE: protein (xi) SEQUENCE DESCRIPTION: SEQ ID NO: 7:

Met Ser Phe Leu Val Ser Glu Glu Leu Ser Phe Arg Ile Pro Val Glu
 1               5                  10                 15

Leu Arg Tyr Glu Thr Cys Asp Pro Tyr Ala Val Arg Leu Thr Phe His
            20                  25                  30

Leu Pro Gly Asp Ala Pro Val Thr Trp Ala Phe Gly Arg Glu Leu Leu
        35                  40                  45
```

Fig. 5 cont.

Ile Asp Gly Gly Pro Arg Pro Cys Gly Asp Gly Asp Val His Ile Ala
    50                  55                  60

Pro Ala Asp Pro Glu Thr Phe Gly Glu Val Leu Ile Arg Leu Gln Val
65                  70                  75                  80

Gly Ser Asp Gln Ala Met Phe Arg Val Gly Thr Ala Pro Leu Val Ala
                85                  90                  95

Phe Leu Asp Arg Thr Asp Lys Ile Val Pro Leu Gly Gln Glu Arg Ser
            100                 105                 110

Leu Ala Asp Phe Asp Ala Leu Leu Asp Glu Ala Leu Asp Arg Ile Leu
            115                 120                 125

Ala Glu Glu Gln Asn Ala Gly
    130                 135

(2) INFORMATION FOR SEQ ID NO: 8:

(i) SEQUENCE CHARACTERISTICS:
       (A) LENGTH: 408 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (vi) ORIGINAL SOURCE:
       (A) ORGANISM: Streptomyces netropsis
       (B) STRAIN: ATCC 23940

(ix) FEATURE:
       (A) NAME/KEY: CDS
       (B) LOCATION: 1..408
       (D) OTHER INFORMATION: /product= "SsgA"
               /gene= "ssgA"

(xi) SEQUENCE DESCRIPTION: SEQ ID NO: 8:

ATG AGC TTC CTC GTC TCC GAG GAG CTC TCC TTC AAG ATC CCA GTC GAA
48
Met Ser Phe Leu Val Ser Glu Glu Leu Ser Phe Lys Ile Pro Val Glu
 1               5                  10                  15

CTG CGA TAC GAG ACC CGG GAT CCC TAC GCG GTG CGG ATG ACC TTC CAC
96
Leu Arg Tyr Glu Thr Arg Asp Pro Tyr Ala Val Arg Met Thr Phe His
                20                  25                  30

CTC CCC GGA GAC GCG CCT GTG ACC TGG GCG TTC GGC CGG GAG CTG CTG
144
Leu Pro Gly Asp Ala Pro Val Thr Trp Ala Phe Gly Arg Glu Leu Leu
            35                  40                  45

CTC GAC GGG ATC AAC CGC CCG AGC GGC GAC GGC GAC GTC CAC ATC GCC
192
Leu Asp Gly Ile Asn Arg Pro Ser Gly Asp Gly Asp Val His Ile Ala
            50                  55                  60

CCG ACC GAC CCC GAG GGC CTG TCG GAC GTC TCC ATC CGG CTC CAG GTG

Fig. 5 cont.

```
240
Pro Thr Asp Pro Glu Gly Leu Ser Asp Val Ser Ile Arg Leu Gln Val
65              70              75              80

GGC GCG GAC CGC GCC CTC TTC CGT GCA GGC GCC CCG CCG CTG GTC GCC
288
Gly Ala Asp Arg Ala Leu Phe Arg Ala Gly Ala Pro Pro Leu Val Ala
                85              90              95

TTC CTC GAC CGC ACG GAC AAG TCG GTG CCG CTC GGT CAG GAA CAG ACT
336
Phe Leu Asp Arg Thr Asp Lys Ser Val Pro Leu Gly Gln Glu Gln Thr
                100             105             110

CTG GGT GAC TTC GAG GAC AGC CTG GAG GCC GCG CTC GGC AAG ATC CTC
384
Leu Gly Asp Phe Glu Asp Ser Leu Glu Ala Ala Leu Gly Lys Ile Leu
                115             120             125

GCC GAG GAG CAG AAC GCC GGC TG
408
Ala Glu Glu Gln Asn Ala Gly
130             135
```

(2) INFORMATION FOR SEQ ID NO: 9:

(i) SEQUENCE CHARACTERISTICS:
        (A) LENGTH: 135 amino acids
        (B) TYPE: amino acid
        (D) TOPOLOGY: linear (ii) MOLECULE TYPE: protein (xi) SEQUENCE DESCRIPTION: SEQ ID NO: 9:

```
Met Ser Phe Leu Val Ser Glu Glu Leu Ser Phe Lys Ile Pro Val Glu
1               5               10              15

Leu Arg Tyr Glu Thr Arg Asp Pro Tyr Ala Val Arg Met Thr Phe His
                20              25              30

Leu Pro Gly Asp Ala Pro Val Thr Trp Ala Phe Gly Arg Glu Leu Leu
                35              40              45

Leu Asp Gly Ile Asn Arg Pro Ser Gly Asp Gly Asp Val His Ile Ala
                50              55              60

Pro Thr Asp Pro Glu Gly Leu Ser Asp Val Ser Ile Arg Leu Gln Val
65              70              75              80

Gly Ala Asp Arg Ala Leu Phe Arg Ala Gly Ala Pro Pro Leu Val Ala
                85              90              95

Phe Leu Asp Arg Thr Asp Lys Ser Val Pro Leu Gly Gln Glu Gln Thr
                100             105             110

Leu Gly Asp Phe Glu Asp Ser Leu Glu Ala Ala Leu Gly Lys Ile Leu
                115             120             125

Ala Glu Glu Gln Asn Ala Gly
130             135
```

(2) INFORMATION FOR SEQ ID NO: 10:

Fig. 5 cont.

(i) SEQUENCE CHARACTERISTICS:
    (A) LENGTH: 34 nucleotides
    (B) TYPE: nucleic acid
    (C) STRANDEDNESS: single
    (D) TOPOLOGY: linear (ii) MOLECULE TYPE: DNA (synthetic)

(vi) ORIGINAL SOURCE:
    (C) INDIVIDUAL PRODUCT: ssg1

(xi) SEQUENCE DESCRIPTION: SEQ ID NO: 10:

GGCGAATTCG AACAGCTACG TGGCGAAGTC GCCA
34

(2) INFORMATION FOR SEQ ID NO: 11:

(i) SEQUENCE CHARACTERISTICS:
        (A) LENGTH: 32 nucleotides
        (B) TYPE: nucleic acid
        (C) STRANDEDNESS: single
        (D) TOPOLOGY: linear (ii) MOLECULE TYPE: DNA (synthetic)

(vi) ORIGINAL SOURCE:
        (C) INDIVIDUAL PRODUCT: ssg2

(xi) SEQUENCE DESCRIPTION: SEQ ID NO: 11:

GTGGGATCCG TGCTCGCGGC GCTGGTCGTC TC
32

(2) INFORMATION FOR SEQ ID NO: 12:

(i) SEQUENCE CHARACTERISTICS:
        (A) LENGTH: 32 nucleotides
        (B) TYPE: nucleic acid
        (C) STRANDEDNESS: single
        (D) TOPOLOGY: linear (ii) MOLECULE TYPE: DNA (synthetic)

(vi) ORIGINAL SOURCE:
        (C) INDIVIDUAL PRODUCT: ssg3

(xi) SEQUENCE DESCRIPTION: SEQ ID NO: 12:

GGGAATTCCA TATGCGCGAG TCGGTTCAAG CA
32

(2) INFORMATION FOR SEQ ID NO: 13:

(i) SEQUENCE CHARACTERISTICS:
        (A) LENGTH: 25 nucleotides
        (B) TYPE: nucleic acid

Fig. 5 cont.

```
        (C) STRANDEDNESS: single
        (D) TOPOLOGY: linear (ii) MOLECULE TYPE: DNA (genomic)

(vi) ORIGINAL SOURCE:
         (C) INDIVIDUAL PRODUCT: ssg4

(xi) SEQUENCE DESCRIPTION; SEQ ID NO: 13:

CCGGTCAGCC GGCGTTCTGC TCCTC
25
```

Fig. 5 cont.

REDUCING BRANCHING AND ENHANCING FRAGMENTATION IN CULTURING FILAMENTOUS MICROORGANISMS

CROSS-REFERENCE TO RELATED APPLICATIONS

This application is a continuation of International Application No. PCT/NL99/00395, filed on 25 Jun. 1999, designating the United States of America (International Publication No. WO 00/00613), the entire contents of which are incorporated by this reference.

TECHNICAL FIELD

The invention relates to industrial microbiology, in particular to fermentation technology and especially to fermentation methods for filamentous microorganisms, in particular filamentous bacteria such as actinomycetes. The invention was made in a research program into mechanisms of growth of streptomycetes.

BACKGROUND

Streptomycetes are Gram-positive, aerobic, filamentous soil bacteria, which belong to the order of actinomycetales. In an early stage of *Streptomyces* growth on a solid medium, spores germinate, and subsequently develop into a vegetative mycelium of multi-nucleoidal and branching hyphae with occasional septums (Chater and Losick, 1996). After environmental signals such as nutrient depletion, aseptate aerial hyphae are formed, growing on the vegetative hyphae, the latter being used as a substrate. Eventually, the aerial hyphae form uninucleoidal cells that develop into hydrophobic spores, which are budded off from the tips of the hyphae. One of the striking features of streptomycetes and other members of the order actinomycetales is their ability to produce a wide variety of secondary metabolites, including many antibiotics, which are produced in temporal relation to the onset of morphological differentiation in surface-grown cultures (Chater, 1989; Miyadoh, 1993). The molecular processes regulating the events that lead to differentiation of *Streptomyces* are presently only superficially understood, although new and interesting insights into the genetics of streptomycetes have come to light (reviewed in Champness and Chater, 1993; Chater, 1993).

Most streptomycetes only sporulate on solid media, while growth in liquid cultures is restricted to the formation of vegetative mycelium. This typically develops into intricate networks of hyphae, among others resulting in pellet formation, with only the most outwardly oriented sections showing high physiological activity, resulting in low yield of the desired product per unit of biomass. Furthermore, because of their filamentous morphology, high density fermentations of biotechnologically interesting streptomycetes often are highly viscous, resulting in a low biomass accumulation due to for instance aeration and mixing problems. From this perspective it is desirable that fragmentation of the mycelium in submerged cultures is stimulated, that branching of the mycelium is reduced and that in general the viscosity of the culture is reduced.

Cell division in all bacteria analysed so far involves the tubulin-like GTP-binding protein FtsZ, which polymerises into a ring at the prospected site of the septum, presumably forming the physical scaffold for the assembly of the cell division apparatus (reviewed in Lutkenhaus and Addinall, 1997). In *Escherichia coli* and *Bacillus* species many factors have been identified that are involved in cell division, but little is known about this process in actinomycetes. Here septum formation does not lead to actual cell division, and while in most bacteria ftsZ is essential, the gene has been shown to be dispensable for mycelial growth in *Streptomyces coelicolor* (McCormick et al., 1994).

In contrast to most actinomycetes, *Streptomyces griseus* shows the ability to sporulate in submerged cultures over a short time period, when grown in defined minimal media (Kendrick and Ensign, 1983; Ensign, 1988). Kawamoto and Ensign (1995a,b) identified a mutation in the gene ssgA that relieved repression of sporulation in rich media. SsgA encodes an acidic protein with a molecular mass of approximately 5 kDa that displays no significant homology to any other known protein in the database; in the sequenced genome of the actinomycetes *Mycobacterium tuberculosis* and *Mycobacterium leprea* no ssgA has been found (http//kiev.physchem.kth.se/mycdb). Overexpression of ssgA resulted in fragmented growth and suppression of sporulation in submerged cultures of *S. griseus*. Fragmented growth was also observed by Kawamoto and Ensign (1995b) by overexpression of ssgA in *S.lividans*, which was supposed to have an ssgA of its own on the basis of weak signals on a Southern blot. In *S.griseus*, Western blot analysis with polyclonal antibodies raised against SsgA revealed that expression of SsgA directly correlates to the onset of submerged sporulation, with the protein appearing shortly before spore formation (Kawamoto et al., 1997). Importantly, although sporulation and production of the antibiotic streptomycin are apparently linked in *S. griseus*, no suppression of streptomycin production was observed. Apparently, regulation of sporulation and antibiotic biosynthesis occur via separate pathways.

DISCLOSURE OF THE INVENTION

The present inventors have shown that the activity of SsgA from *S. griseus* is not limited to the organism in which it is found. The activity can advantageously be transferred to other organisms, thereby allowing more fragmented growth and/or reduced branching and/or reduced viscosity of the culture of many filamentous microorganisms, in particular actinomycetes and steptomycetes. This special growth behaviour is observed in a wide variety of culture mediums. It is particularly surprising, that organisms in which a significant endogenous ssgA-like activity is not detectable still respond to the presence of the product of the ssgA gene. Thus we demonstrate that introduction of ssgA into various bacteria, in particular actinomycetes that lack significant endogenous ssgA activity results in suppressed branching and enhanced fragmentation of the mycelium in liquid culture, resulting in significantly lower viscosity of culture broths. In addition to autonomously replicating plasmids containing constitutively expressed ssgA, we devised a system that allows easy integration of the gene in the chromosome, with the advantage of high stability combined to that of independent regulation of ssgA.

Thus the invention now provides a method for producing a filamentous bacterium showing reduced branching during growth, particularly growth in a liquid medium, comprising providing such a bacterium with the capability of having or expressing heterologous SsgA activity, which activity in *Streptomyces Griseus* is encoded by an ssgA gene having the sequence:

```
  1 ATGCGCGAGTCGGTTCAAGCAGAGGTCATGATGAGCTTCCTCGTCTCCGA  (SEQ ID NO: 1)

51 GGAGCTCTCGTTCCGTATTCCGGTGGAGCTCCGATACGAGGTCGGCGATC

101 CGTATGCCATCCGGATGACGTTCCACCTTCCCGGCGATGCCCCTGTGACC

151 TGGGCGTTCGGCCGCGAGCTGCTGCTGGACGGGCTCAACAGCCCGAGCGG

201 CGACGGCGATGTGCACATCGGCCCGACCGAGCCCGAGGGCCTCGGAGATG

251 TCCACATCCGGCTCCAGGTCGGCGCGGACCGTGCGCTGTTCCGGGCGGGG

301 ACGGCACCGCTGGTGGCGTTCCTCGACCGGACGGACAAGCTCGTGCCGCT

351 CGGCCAGGAGCACACGCTGGGTGACTTCGACGGCAACCTGGAGGACGCAC

401 TGGGCCGCATCCTCGCCCAGGAGCAGAACGCCGGCTGA.
```

DETAILED DESCRIPTION OF THE INVENTION

As explained above the presence of additional SsgA activity, in particular heterologous SsgA-activity (meaning activity not in a form as present in the microorganism in nature), irrespective of the presence or absence of endogenous SsgA activity, leads to enhanced fragmentation, reduced branching and thus reduced viscosity in a wide range of culture mediums. The activity may be provided in any suitable manner, but it is preferred that the activity is provided by transfecting or transforming said filamentous bactrium with additional genetic information encoding said activity. Examples of such methods are presented hereinbelow, but the art of genetic engineering of bacteria is so well advanced that persons skilled in the art will be able to come up with numerous methods and variations thereof to provide an intended filamentous bacterium with a gene encoding SsgA-like activity. SsgA-like activity is functionally defined as the ability to enhance septation, fragmentation and/or reduce branching in (typically) submerged cultures of filamentous microorganisms, in particular bacteria, more specifically actinomycetes. The activity of other ssgA-like genes or fragments of ssgA genes or derivatives of ssgA genes which are within the invention must be functionally the same, but that does not mean that the amount of activity per molecule needs to be the same. SsgA-like activity is thus defined as similar in kind, though not necessarily in amount. Other genes encoding such SsgA activity than the genes disclosed herein can be obtained without departing from the invention by applying routine hybridization and/or amplification techniques. Means and methods for expressing such genes are well known in the art so that there is no need to go into detail here regarding cloning vectors, expression vectors, (inducible) promoters, enhancers, repressors, restriction enzymes, etc. etc. For stability of the presence of the added SsgA-activity to the bacterium, in particular for application in large scale fementations, it is however preferred that the genetic information encoding the additional SsgA activity is integrated into the host cell genome. In this case typically the genetic information will be in the form of DNA. However, neither RNA, heteroduplexes or even PNAs are excluded from the present invention as means to provide the additional genetic information to a microorganism. The invention is preferably applied in the field of filamentous bacteria, in particular actinomycetes and most specifically to streptomycetes. In these embodiments in particular it is preferred to apply ssgA genes derived from actinomycetes, especially from other actinomycetes than the one to be altered in growth characteristics. This of course is automatically the case in a bacterium that does not have SsgA activity to any significant amount itself. Using a gene from a related organism enhances the compatibility of the expression machinery of the host with the gene. Thus it is particularly preferred to provide a Streptomyces with an ssgA (-like) gene from a different Streptomyces. SsgA genes are found in *Streptomyces griseus, Streptomyces collinus, Streptomyces albus, Streptomyces goldeniensis* and *Streptomyces netropsis*. It is preferred to provide Streptomyces strains not having significant endogenous SsgA activity with a gene from the earlier mentioned strains.

It is useful to ensure that said additional SsgA activity is inducible or repressible with a signal. In this way the growth characteristics of the bacteria can be modified at will. Of course the final goal of the present invention is to enhance the production of useful products by the microorganisms by modifying the microorganisms according to the invention. Useful products produced by or through microorganisms according to the invention include so called secondary metabolites, typically antibiotics or antitumour agents, but also immunosuppressive agents, hypocholesterolemic agents, enzyme inhibitors, antimigraine agents, herbicides, antiparasitic agents, ruminant growth promoters, bioinsecticides, receptor (ant)agonists, hetreolgous proteins or even simple biomass. In the case of Streptomycetes such a useful product is typically an antibiotic. It is thus therefore preferred according to the invention to modify antibiotic producing strains of Streptomyces, particularly those not displaying a significant endogenous SsgA like activity, with genetic information encoding SsgA activity. On the other hand the invention can also be very suitably applied to Streptomycetes or other microorganisms expressing heterologous proteins (or overexpressing homologous/endogenous proteins).

For ease of production it is preferred that the useful product, said antibiotic or said protein, is secreted by said bacterium. The protein to be expressed may very well be a protein involved in the pathway of making a useful product such as an antibiotic, so that this production can be further enhanced on top of the improvement by the reduced fragmentation, etc. In that case it would be very suitable to combine the two genes on one vehicle for introduction into the bacterium. The bacteria resulting from the methods according to the invention are of course also part of the invention. They have additional SsgA activity (or are capable of expressing such activity) and they thereby will typically have different growth characteristics than the unmodified microorganisms when said SsgA activity is present. Thus the invention also provides a filamentous bacterium obtainable by a method according to invention. Preferred microorganisms according to the invention are actinomycetes and typically streptomycetes. As stated above it is an important goal of the present invention to improve fermentative production of useful products such as antibiotics. Thus the invention also provides a method for producing an antibiotic or a useful protein comprising culturing a filamentous bacterium according to the invention and harvesting said antibiotic or protein from said culture. The advantages of the invention are most clear when the method of culturing is submerged culture. The invention will be explained in more detail in the following experimental part.

Experimental procedures

Bacterial strains, culture conditions and plasmids

E. coli K-12 strains JM109 (Messing et al., 1981), and ET12567 (MacNeil, et al., 1992) were used for routine sub-cloning. The strains were grown and transformed by standard procedures (Sambrook et al., 1989); transformants were selected in L broth containing 1% (w/v) glucose, and ampicillin at a final concentration of 200 μg ml$^{-1}$. L broth with 1% glucose and 30 μg ml$^-$ chloramphenicol was used to grow ET12567.

Streptomyces coelicolor A3(2) M145 and Streptomyces lividans 1326 (Hopwood et al., 1985) were used for transformation and propagation of Streptomyces plasmids. Protoplast preparation and transformation were performed as described by Hopwood et al. (1985). SFM medium (mannitol, 20 g l$^{-1}$; soya flour, 20 g l$^{-1}$; agar, 20 g l$^{-1}$, dissolved in tap water) is a modified version of that reported by Hobbs et al. (1989) and was used to make spore suspensions. R2YE (Hopwood et al., 1985) was used for regenerating protoplasts and, after addition of the appropriate antibiotic, for selecting recombinants.

For liquid culturing of Streptomyces we used YEME medium (Hopwood et al., 1985), Tryptone soy broth (Difco) containing 10% sucrose (designated TSBS), or standard minimal medium (MM; Hopwood et al.) with 1% mannitol as carbon source.

Strains used for screening of ssgA were Streptomyces albus G (ATCC 3004), Streptomyces ambofaciens (ATCC 23877), Streptomyces antibioticus (ATCC8663), Streptomyces clavuligerus (ATCC 27064), Streptomyces coelicolor M145, Streptomyces collinus (DSM 40733), Streptomyces fradiae (CBS 498.68), Streptomyces goldeniensis (ATCC 21386), Streptomyces griseus (ATCC 23345), Streptomyces kasugaensis (DSM 40819), Streptomyces lividans, Streptomyces mobaraensis (ATCC 25365), Streptomyces netropsis (formerly Streptoverticilium netropsis; ATCC 23940), Streptomyces ramocissmus (ATCC 27529), and the actinomycetes Nocardia lactamdurans (ATCC 27382), Planobispora rosea (ATCC 53773), Saccharopolyspora erythraea (NRRL 2338).

Plasmids pUC18 (Yanisch-Perron et al., 1985), pIJ2925 (Janssen and Bibb, 1993), and pSET152 (Bierman et al., 1992) were used for cloning experiments. While pSET152 is a conjugative shuttle plasmid, in the experiments described in this study the plasmid and its derivatives were introduced by standard protoplast transformation.

pIJ486 (Ward et al., 1986) and the E. coli/Streptomyces shuttle vector pWHM3 (Vara et al.) as high copy-number vectors (approximately 50–100 copies per chromosome) in S. coelicolor. An expression vector, designated pWHM3-E, was constructed by cloning the 300 bp EcoRI/BamHI fragment containing the ermB promoter (Bibb et al., 1994) into pWHM3. Standard procedures were used to isolate plasmid DNA from E. coli (Sambrook et al., 1989), and to isolate plasmid and total DNA from Streptomyces (Hopwood et al., 1985).

PCR conditions

Polymerase chain reactions (PCRs) were performed in a minicycler (MJ Research, Watertown, Mass.), using Pfu polymerase (Stratagene, La Jolla, La.), and the buffer provided by the supplier, in the presence of 5% (v/v) DMSO and 200 mM dNTP. No additional $Mg^{++}$ was added to the reaction mixture. The following PCR program was used: 30 cycles of 45 seconds melting at 94° C., 1 minute annealing at 54° C., and 90 seconds extension at 72° C., followed by an additional 10 minutes at 72° C.

Constructs for expression of sagA

A 750 bp DNA fragment containing the ssgA gene (Accession D50051) was amplified from the Streptomyces griseus chromosome by PCR, using primers ssg1 and ssg2 (Table 1). The PCR fragment was cloned as an EcoRI-BamHI fragment in pIJ2925, and further into pWHM3, pWHM3-E, and pSET152, resulting in pGWS1, pGWS2, pGWS3, and pGWS4, respectively (Table 1). For pGWS1 and pGWS3, see also FIG. 1. The S. coelicolor strain with pGWS4 integrated in the attP site on the chromosome was designated S. coelicolor GSA1. For pGWS1, pGWS3, and pGWS4 we also made derivatives in which the upstream region of S. griseus ssgA was replaced by that of S. ramocissmus tuf1 (Vijgenboom et al., 1994), which is known to be very efficiently recognized by ribosomes and hence typically results in higher expression; these were designated pGWS1-SD, pGWS3-SD, and pGWS4-SD, respectively.

Southern hybridization and probes

Genomic DNAs used for Southern analysis were isolated according to the method described by Hopwood et al. (1985). For high-resolution hybridization experiments, to investigate the presence of ssgA in various actinomycetes, genomic DNA was digested with the appropriate enzymes and separated electrophoretically on a 0.7% agarose gel in TAE buffer, using the Gibco BRL 1 kb ladder as DNA size markers. Agarose gels were pretreated and subsequently blotted on Hybond-N$^+$ nylon membranes (Amersham) using 20x SSC buffer as the transfer buffer, basically according to Sambrook et al. (1989). Hybridization and washing conditions were described previously (van Wezel et al., 1991). Stripping of blots was done by 30 minutes incubation in 0.4 N NaOH at 65° C. and subsequent incubation in 0.1x SSC/0.25 M Tris (pH 6.5). The total removal of the probe was checked by overnight exposure of an X-ray film.

For recognition of ssgA in Southern hybridization experiments the 580 bp insert from pGWS5 was [$^{32}$P]-labelled by the random-prime method (Feinberg and Vogelstein, 1983).

Northern Analysis

RNA samples (approximately 20 μg) were glyoxylated, run in a 1.2% agarose gel in 20 mM sodium phosphate buffer (pH 6.7), and blotted onto Hybond N$^+$ nylon membranes using 30 mM sodium phosphate (pH 6.7) as the blotting buffer. Hybridization with the S. netropsis ssgA gene was carried out in 5xSSC, 0.1% SDS, and 1x Blocking reagent (Boehringer Mannheim), O/N at 65° C. Washing occurred until the background was sufficiently low.

Nuclease S1 mapping

For nuclease S1 protection assays, 50 nmol of $^{32}$p-end-labelled probe (≈10$^4$ Cerenkov counts min$^{-1}$) was hybridized to 20 μg of RNA in 3M Na-TCA at 45° C. overnight after denaturation at 70° C. All subsequent steps were carried out as described previously (Strauch et al., 1991).

Computer analysis

The BLAST search engines BlastN, BlastP, and BlastX (Altschul et al., 1990) were used to perform database searches, and the Wisconsin GCG Package (Devereux et al., 1984) for sequence alignments and protein analysis.

Results

SsgA is a unique protein that does not belong to any known protein family

Extensive searches with *S. griseus* SsgA of both the translated nucleotide database and the protein database using the BLAST search engines BLASTX and BLASTP resulted in one relevant hit, namely a partial sequence of *Streptomyces albus* G DNA (Accession M28303) that apparently encodes part of SsgA. This DNA was identified upstream of a β-lactamase gene (Dehottay et al., 1987), and apparently encodes 67 residues of a putative protein with 86% aa identity to aa 18–84 of *S. griseus* SsgA. The lack of the C-terminal half of the gene suggests that the cloning of this ssgA homologue was probably coincidental and the result of a cloning artifact. The cloning and sequencing of the complete gene is described below.

Cloning of *S. griseus* ssgA by PCR

The sequence of *S. griseus* ssgA was published by Kawamoto and Ensign (1995b), and deposited in the EMBL/GENBANK database (D50051). In a recent update the translational start codon was proposed 30 nt downstream of the originally indicated start codon. This ambiguity does not influence the outcome of our experiments. On the basis of protein electrophoresis (SDS PAGE) experiments using over-expressed SsgA and in view of the optimal spacing between ribosome binding sequence and start codon, we believe that the ATG of the $11^{th}$ triplet of the originally proposed reading frame represents the correct translational start codon (data not shown). This is also supported by phylogenetic evidence from the ssgA homologous mentioned below.

The 750 bp DNA fragment generated by PCR amplification of *S. griseus* chromosomal DNA using oligonucleotides ssg1 and ssg2 was cloned into pIJ2925, resulting in pGWS1 (Table 1). Restriction site and sequence analysis confirmed that the fragment indeed contained ssgA.

Southern hybridization reveals ssgA in a limited number of streptomycetes

Figure 2:
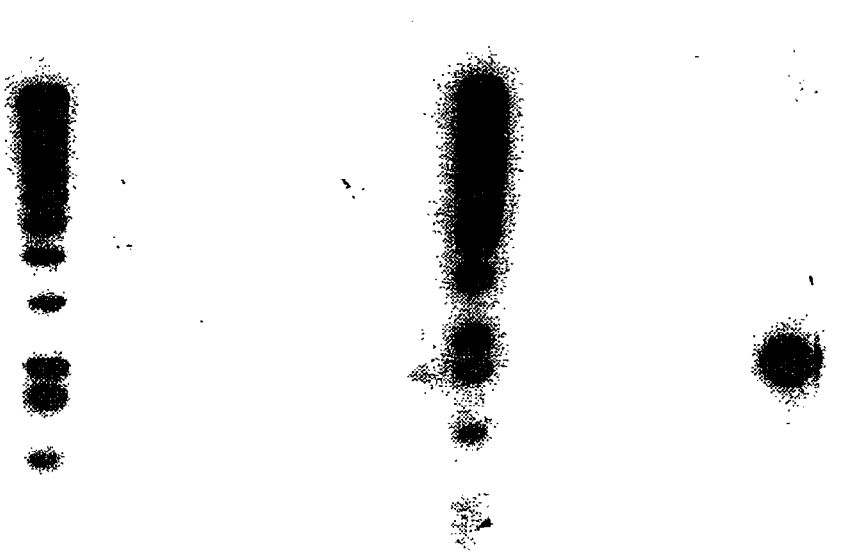
Figure 2:

Genomic DNAs isolated from several actinomycetes (see legend to FIG. 2) was digested with BamHI and PstI, submitted to agarose gel electrophoresis and hybridised with the 580 bp insert from pGWS5 harbouring *S. griseus* ssgA, under conditions of low stringency to identify all genes with at least remote similarity to ssgA. One hybridising band was observed in the lanes containing *S. collinus*, *S. albus*, *S. goldeniensis*, and *S. griseus* genomic DNAs, and two bands of equal intensity in the lane containing *S. netropsis* DNA (FIG. 2). Under stringency conditions allowing the detection of genes with at least 65% homology to *S. griseus* ssgA, we failed to detect a band corresponding to ssgA in all other Streptomyces species, including *S. coelicolor* and *S. lividans*, in contrast to a previous Southern analysis by Kawamoto and Ensign (1995b), who used a probe that included ssgA flanking sequences from an unrelated genomic DNA region. The duplicity of the signal corresponding to ssgA in *S. netropsis* was due to a BamHI restiction site in the gene, as can be deduced from the DNA sequence. We also could not detect an sagA homologue in any of the other actinomycetes checked, namely *Nocardia lactamdurans*, *Planobispora rosea*, and *Saccharopolyspora erythraea*.

Cloning and sequencing of saga homologues from other streptamycetes

Genomic DNA fragments harbouring ssgA homologues from three streptomycetes, namely *S. albus*, *S. qoldeniensis*, and *S. netropsis*, were amplified by PCR, using oligonucleotides ssg3 and ssg4. These fragments were cloned as EcoRI/BamHI fragments into pIJ2925, and the DNA sequence was determined. Table 2 shows the similarities of the ssgA genes and the deduced amino acid sequences. Interestingly, the *S. netropsis* and *S. griseus* ssgA gene products share more than 86% identical amino acids (90% similar), which is high in comparison to 79% (85%) for *S. goldeniensis* SsgA and, strikingly, a poor 63% (71%) for *S. albus* SsgA.

*S. griseus* and *S. netropsis* sporulate in liquid cultures

The morphology of the streptomycetes and actinomycetes discussed in this paper was checked by various microscopic techniques. To this purpose, the strains were grown in complex (TSBS) or minimal (MM) liquid medium for three days, and growth characteristics monitored. From these experiments it appeared that only *S. griseus* and *S. netropsis* produced abundant spores in liquid cultures, while *S. goldeniensis* and *S. collinus* showed unusual thickening of the tips of the hyphae, but failed to sporulate under the chosen conditions. Interestingly, while *S. griseus* sporulated only in MM, as was already reported by Kendrick and Ensign (1983), *S. netropsis* sporulated abundantly in TSBS as well as in MM. We believe that the relation between sporulation and the expression of SsgA is of particular interest.

Transcription analysis

Transcription analysis by nuclease S1 mapping showed an accumulation of ssgA transcripts in *S. griseus* and *S. netropsis* after nutritional shift-down and at the onset of sporulation. *S. coelicolor* did not sporulate under these conditions. Northern analysis of RNA isolated from *S. coelicolor* M145 after nutritional shift-down or normal growth was carried out, using the *S. netropsis* sagA gene as the probe. Expectedly, this did not reveal ssgA transcripts in *S. coelicolor*.

Expression of ssgA in *S. coelicolor* M145 results in reduced branching of the hyphae and fragmented growth The insert of pGWS1 was cloned into pWHM3 and pWHM3-E, multicopy shuttle vectors that replicate in *E. coli* and Streptomyces. The resulting plasmids pGWS2 and pGWS3 (Table 1) were introduced into *S. coelicolor* M145 and correct recombinants were selected by checking the insert lengths of the plasmids. In a control experiment we used pWHM3-E transformants.

Figure 3:
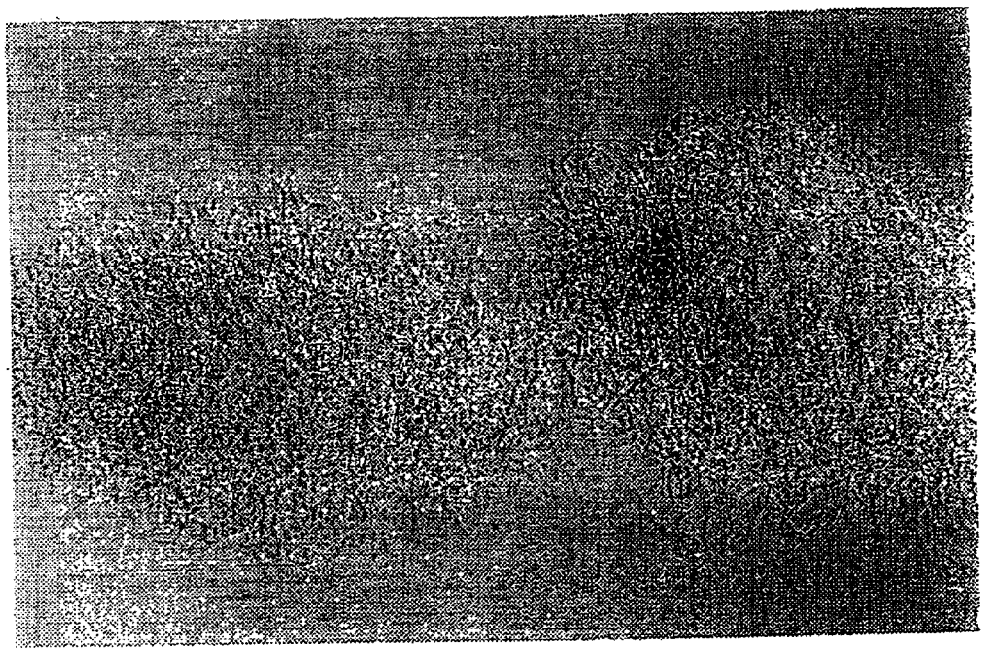
Figure 3:
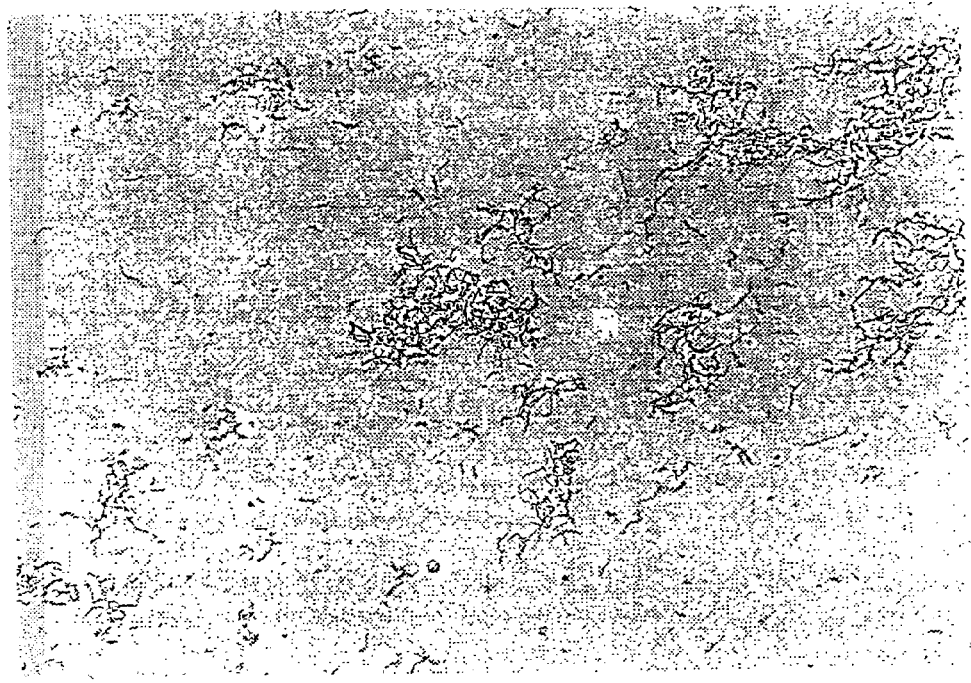
Figure 4:
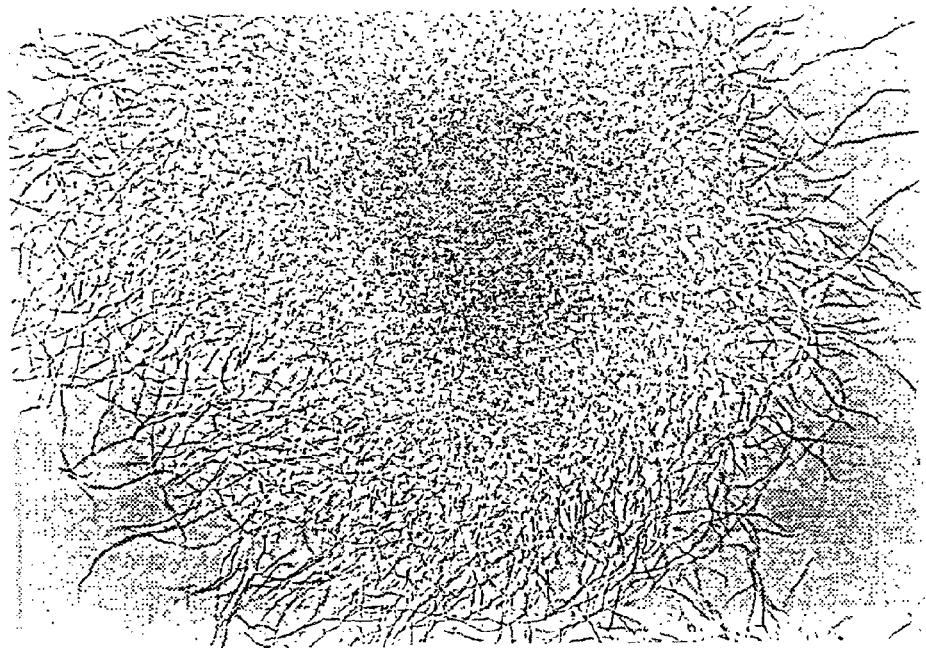
Figure 4:
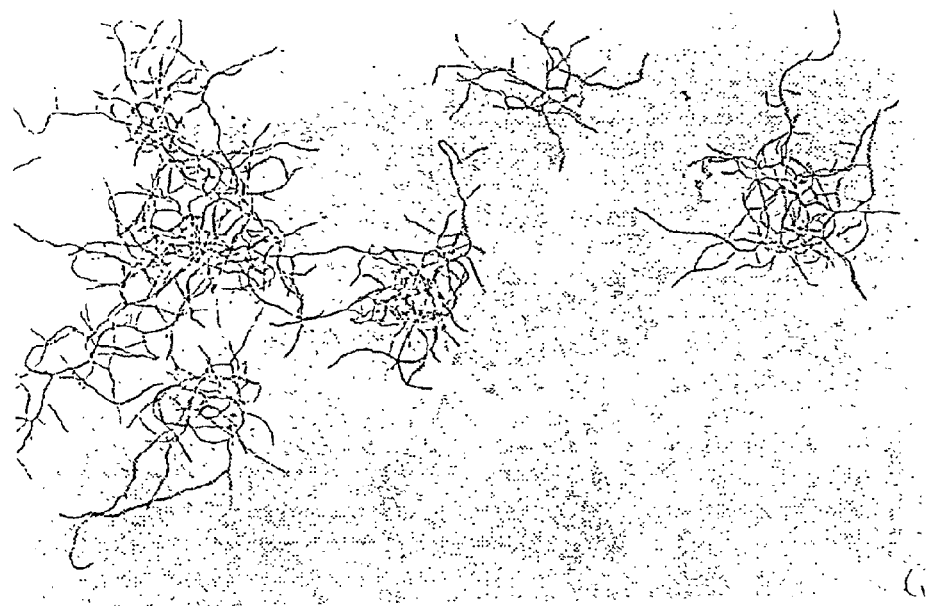

Transformants containing pWHM3-E (without ssgA) or pGWS2 showed little or no altered morphology in the complex liquid media TSBS, YEME, nor in minimal medium (MM), as judged by phase-contrast microscopy (FIG. 3A). However, hyphae of transformants containing pGWS3 showed strongly reduced branching in complex and minimal medium cultures, resulting in clearly less dense mycelial lumps (FIG. 3B). The vegetative hyphae not only show limited branching, but many of the branches are less than a micron in length. When pGWS3-SD was used instead of pGWS3, the effect was even stronger, with small fragments appearing after approximately 30 hrs, which increased over time (FIG. 4). While MM cultures of *S. coelicolor* typically result in very large mycelial lumps that sediment rapidly (virtually all mycelium precipitates within one minute when shaking was stopped), MM cultures containing pGWS3-SD transformants showed significantly reduced sedimentation rates, with the majority of the mycelium failing to sediment within five minutes after shaking of the cultures was stopped.

Constitutive expression of chromosomally-integrated saga also results in fragmented growth The insert of pGWS3 and pGWS3-SD was cloned in pSET152, a conjugative *E. coli/Streptomyces* shuttle vector, resulting in pGWS4 and pGWS4-SD, respectively. These plasmids were introduced into *S. coelicolor* M145 by standard protoplast transformation, and transformants selected by overlay of the transformation plates with apramycin. Chromosomal integration was checked by Southern analysis, and presence of the complete gene confirmed by PCR using oligonucleotides ssg1 and ssg2. The pGWS4 and pGWS4-SD integrants were designated GSA1 and GSA2. *S. coelicolor* M145 harbouring pSET152 without ssgA was used as control strain.

Figure 3C:
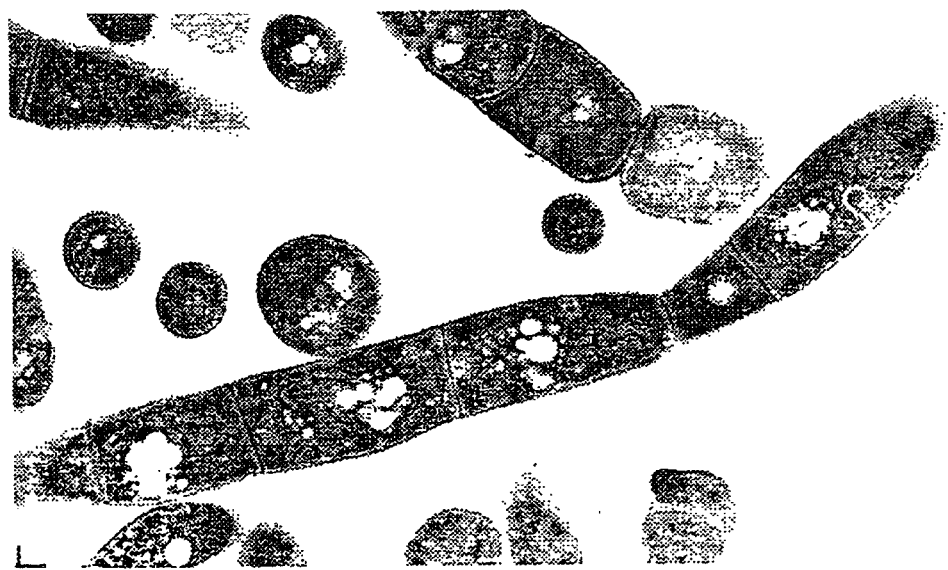
Figure 3C:
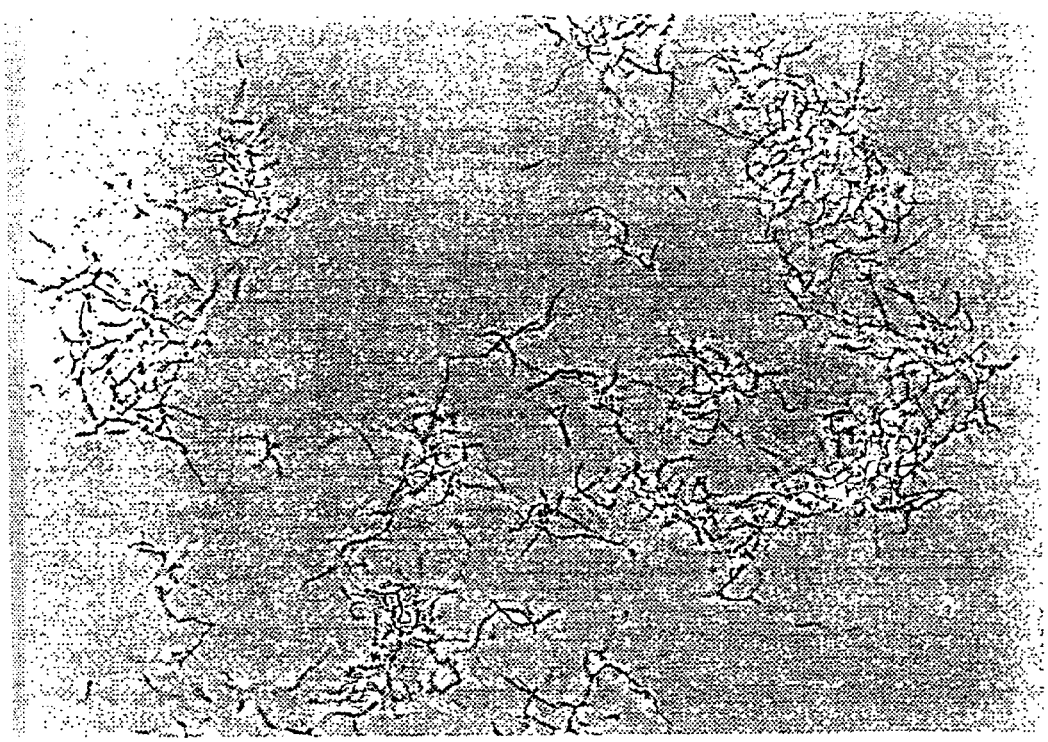

While recombinants containing pSET152 displayed wild-type phenotype, with large mycelial lumps and very few smaller fragments, GSAL showed limited branching, while the phenotype of GSA2 is much similar to that of *S. coelicolor* harbouring pGWS3-SD, with strongly limited branching, frequent septation and fragmented growth (FIG. 3C). This shows that *S. griseus* ssgA integrated in the *S. coeli color* chromosome can be expressed at a level high enough to allow fragmentation of *S. coelicolor* mycelium in complex and minimal liquid cultures.

High level expression of saga in other actinomycetes

The ssgA expression vectors pGWS3-SD and pGWS4 were introduced in *S. lividans, S. clavuligerus,* and *Sacch. erythraea,* to test the effect of SsgA on the morphology of strains other than *S. coelicolor.* Expression in *S. lividans* using pGWS3-SD or pGWS4 led to a phenotype much similar to that of *S. coelicolor* harbouring the same plasmids, as was expected since *S. lividans* and *S. coelicolor* are strongly related streptomycetes. Interestingly, expression of SsgA in both *S. clavuligerus* and *Sacch. erythraea* also resulted in reduced branching and increased fragmentation in liquid cultures (FIG. 4), even though morphology of these strains is different from that of *S. coelicolor.*

Thus, it appears that overproduction of SsgA has a strong effect on mycelium morphology in submerged cultures of actinomycetes, irrespective of the presence or absence of endogenous ssgA-like activities, with the vegetative hyphae showing much enhanced septation and restricted branching. Furthermore, the ageing cultures showed an increasing degree of fragmentation, resulting in higher culture densities and lower viscosity of recombinant streptomycetes expressing ssgA. Comparison of the phenotypes of the two categories of Streptomyces strains, namely those displaying ssgA activity and those without a significant level, is currently in progress, and could give us more insight into the role of SsgA in Streptomyces physiology.

FIGURE LEGENDS

FIG. 1. Some of the ssgA constructs. Arrows show direction of ssgA. $P_{armk}$, ermE promoter; $P_{T7}$, T7 promoter. Solid lines represent ssgA DNA, broken lines represent plasmid DNA.

FIG. 2. Southern hybridization for the detection of ssgA in actinomycetes. All numbered lanes contain BamHI/PstI-digested chromomal DNA. Marker lanes (M) contain 1 kb DNA ladder. Blots were hybridized with the 580 bp insert from pGWS5 as probe, and subsequently with a small amount of radioactively labelled 1 kb ladder. A. Lanes: 1. *S. coelicolor* 2. *S. lividans* 1326 3. *S. lividans* TK24 4. *S. griseofuscus* 5. *S. fradiae* 6. *S. ramocissimus* 7. *S. collinus* 8. *S. kasugaensis* 9. *S. antibioticus* 10. *Sacch. erythraea* 11. *N. lactamdurans* 12. *P. rosea* 13. *S. griseus* B. Lanes: 1. *S. albus* 2. *S. ambofaciens* 3. *S. coelicolor* 4. *S. clavuligerus* 5. *S. collinus* 6. *Sacch. erythraea* 7. *S. goldeniensis* 8. *S. mobaraensis* 9. *S. netropsis* 10. *P. rosea*

FIG. 3. Phase-contrast microscopy of *S. coelicolor* M145 containing (A) pGWS2, and (B) pGWS3 at 200x magnification, (C) *S. coelicolor* M145 with chromosomally integrated pGWS4 (magnification 500x); upper part, details revealed by electron microscopy (magnification 10.000x)

FIG. 4. Phase-contrast microscopy of *S. clavuligerus* ATCC 27064. (A) *S. clavuligerus* (wild type), (B) Recombinant *S. clavuligerus* containing pGWS4-SD.

FIG. 5. Sequences of different ssgA genes and proteins from different strains and oligonucleotides.

TABLE 1

Oligonucleotides and ssgA constructs. Nucleotide positions refer to the location of the primers in respect to the first nucleotide (+1) of the ATG translational start codon of ssgA. Underlined sequences indicate non-homologous sequences added to create restriction sites (in italics) at the ends of the PCR fragments.

| primer | Oligonucleotides | | Nucl. Pos. |
|---|---|---|---|
| ssg1 | 5' GGCGAATTCGAACAGCTACGTGGCGAAGTCGCCA3' (nucleotides 1–9 are non-homologous, added nucleotides to create an EcoRI site at nucleotides 5–9) | (SEQ ID NO: 10) | −194/−170 |
| ssg2 | 5' GTGGGATCCGTGCTCGCGGCGCTGGTCGTCTC 3' (nucleotides 1–9 are non-homologous, added nucleotides to create a BamHI site at nucleotides 4–9) | (SEQ ID NO: 11) | +539/+517 |
| ssg3 | GGGAATTCCATATGCGCGAGTCGGTTCAAGCA 3' (nucleotides 1–11 are non-homologous, added nucleotides to create an EcoRI and NdeI sites at nucleotides 3–14) | (SEQ ID NO: 12) | −30/−10 |
| ssg4 | 5' CCGGTCAGCCGGCGTTCTGCTCCTC 3' | (SEQ ID NO: 13) | +412/388 |
| Plasmids | | | |
| pIJ2925 | Derivative of pUC19, with BglII sites flanking the slightly altered multiple cloning site. | | Janssen and Bibb, 1993 |

TABLE 1-continued

Oligonucleotides and ssgA constructs. Nucleotide positions refer to the location of the primers in respect to the first nucleotide (+1) of the ATG translational start codon of ssgA. Underlined sequences indicate non-homologous sequences added to create restriction sites (in italics) at the ends of the PCR fragments.

| | | |
|---|---|---|
| pWHM3 | Multi-copy E. coli/Streptomyces shuttle vector. Carries thiostrepton resistance marker | Vara et al. |
| pWHM3-E | pWHM3 with the 300 bp fragment containing the constitutive ermE promoter for gene expression | this study |
| pSET152 | E. coli/Streptamyces shuttle vector that allows integration in the _C31 attachment site on the Streptomyces chromosome. Carries apramycin resistance marker. | Bierman et al, 1992 |
| pGWS1 | pIJ2925 containing the 750 bp ssgA PCR (ssg1/ssg2) product | this study |
| pGWS1-SD | pGWS1 with the upstream region of ssgA replaced by nt −1/−70 of S. ramocissimus tuf1 | this study |
| pGWS2 | pWHM3 containing the EcoRI/HindIII insert from pGWS1 | this study |
| pGWS3 | pWHM3-E containing the BglII/HindIII insert from pGWS1 | this study |
| pGWS3-SD | pWHM3-E containing the BglII/HindIII insert from pGWS1-SD | this study |
| pGWS4 | pSET152 containing the EcoRI/PstI insert from pGWS3 | this study |
| pGWS4-SD | pSET152 containing the EcoRI/PstI insert from pGWS3-SD | this study |
| pGWS5 | pIJ2925 containing the 580 bp ssgA PCR (ssg3/ssg2) product cloned EcoRI/BamHI. | |

TABLE 2

DNA and deduced protein sequence homologies of ssgA homologues. Above the diagonal: DNA sequence identities (%). Below the diagonal: protein sequence identities (similarities between brackets).

| | S. albus | S. goldeniensis | S. griseus | S. netropsis |
|---|---|---|---|---|
| S. albus | X | 75.2 | 74.5 | 72.3 |
| S. goldeniensis | 71.3 (75.7) | X | 77.5 | 75.7 |
| S. griseus | 66.2 (71.3) | 78.7 (85.3) | X | 83.3 |
| S. netropsis | 63.2 (70.6) | 77.9 (83.8) | 86.0 (90.4) | X |

REFERENCES

Bibb, M. J., White, J., Ward, J. M., and Janssen, G. R. (1994) The mRNA for the 23S rRNA methylase encoded by the ermE gene of Saccharopolyspora exythraea is translated in the absence of a conventional ribosome-binding site. Mol. Microbiol. 14: 533–45.

Bierman, M., R. Logan, K. Obrien, E. T. Seno, R. N. Rao, and Schoner, B. E. (1992) Plasmid cloning vectors for the conjugal transfer of DNA from Escherichia coli to Streptomyces spp. Gene 116: 43–49.

Chater, K. F., and Losick, R. (1996) The mycelial life-style of Streptomyces coelicolor A3 (2) and its relatives. In J. H. Shapiro and M. Dworkin (ed.), Bacteria as Multicellular Organisms. Oxford University Press, New York.

Dehottay, P., Dusart, J., De Meester, F., Joris, B., van Beeumen, J., Erpicum, T., Frere, J.-M., and Ghuysen, J.-M. (1987) Nucleotide sequence of the gene encoding the Streptomyces albus G β-lactamase gene. Eur. J. Biochem. 166: 345–350.

Devereux, J., Haeberli, P., and Smithies, O. 1984. A comprehensive set of sequence analysis programs for the VAX. Nucleic Acids Res. 12: 387–395.

Ensign, J. C. (1988) Physiological regulation of sporulation of Streptomyces griseus. In Y. Okami, T. Beppu, and H. Ogawara (eds.), Biology of Actinomycetes 1988, pp. 308–315. Tokyo, Japan Scientific Societies Press.

Feinberg, A. P., and Vogelstein, B. (1983) A technique for radiolabeling of DNA restriction endonuclease fragments to high specific activity. Anal. Biochem. 132: 6–13.

Hobbs, G., Frazer, C. M., Gardner, D. C. J., Flett, F., and Oliver, S. G. (1989) Dispersed growth of Streptomyces in liquid culture. Appl Microbiol Biotechnol 31:272–277.

Hopwood, D. A., Bibb, M. J., Chater, K. F., Kieser, T., Bruton, C. J., Kieser, H. M., Lydiate, D. J., Smith, C., Ward, J. M., and Schrempf, H. (1985) Genetic manipulation of Streptomyces: a laboratory manual. John Innes Foundation, Norwich, U. K.

Janssen, G. R., and Bibb, M. J. (1993) Derivatives of pUC18 is that have BglII sites flanking a modified multiple cloning site and that retain the ability to identify recombinant clones by visual screening of Escherichia coli colonies. Gene 124: 133–134.

Kawamoto, S., and Ensign, J. C. (1995a) Isolation of mutants of Streptomyces griseus that sporulate in nutrient rich media: cloning of DNA fragments that suppress the mutations. Actinomycetologica 9: 124–135.

Kawamoto, S., and Ensign, J. C. (1995b) Cloning and characterization of a gene involved in regulation and sporulation and cell division in Streptomyces griseus. Actinomycetologica 9: 136–151.

Kawamoto, S., Watanabe, H., Hesketh, A., Ensign, J. C., and Ochi, K. (1997) Expression of the ssgA gene product, associated with sporulation and cell division in Streptomyces griseus. Microbiology 143: 1077–1086.

Kendrick, K., and Ensign, J. C. (1983) Sporulation of Streptomyces griseus in submerged culture. J. Bacteriol. 155: 357–366.

Lutkenhaus, J., and Addinall, S. G. (1997) Bacterial cell division and the Z ring. Annu Rev. Biochem. 66: 993–116.

MacNeil, D. J., Gewain, K. M., Ruby, C. L., Dezeny, G., Gibbons, P. H., and MacNeil, T. (1992) Analysis of Streptomyces avermitilis genes required for avermectin biosynthesis utilising a novel integration vector. Gene 111: 1–68.

McCarthy, A. J., and Williams, S. T. (1992) Actinomycetes as agents of biodegradation in the environment—a review. Gene 115: 189–192.

McCormick, J. R., Su, E. P., Driks, A., and Losick, R. (1994) growth and viability of Streptomyces coelicolor mutant for the cell division gene ftsZ. Mol. Microbiol. 14: 243–254.

Messing, J., Crea, R., and Seeburg, P. H. (1981) A system for shotgun DNA sequencing. Nucleic Acids Res 9: 309–321.

Miyadoh, S. (1993) Research on antibiotic screening in Japan over the last decade: a producing microorganisms approach. Actinomycetol 7: 100–106.

Redenbach, M., Kieser, H. M., Denapaite, D., Eichner, A., Cullum, J., Kinashi, H., and Hopwood, D. A. (1996) A set of ordered cosmids and a detailed genetic and physical map for the 8 Mb Streptomyces coelicolor A3 (2) chromosome. *Mol Microbiol.*

Sambrook, J., Fritsch, E. F., and Maniatis, T. (1989) Molecular cloning: a laboratory manual. Cold Spring Harbor Laboratory, Cold Spring Harbor, N.Y.

Strauch, E., Takano, E., Baylis, H. A., and Bibb, M. J. (1991) The stringent response in Streptomyces coelicolor A3 (2). *Mol. Microbiol.* 5: 289–298.

Strohl, W. R. (1992) Compilation and analysis of DNA sequences associated with apparent streptomycete promoters. *Nucleic Acids Res* 20: 961–974.

van Wezel, G. P., Vijgenboom, E., and Bosch, L. (1991) A comparative study of the ribosomal RNA operons of *Streptomyces coelicolor* A3 (2) and sequence analysis of rrnA. *Nucleic Acids Res* 19: 4399–4403.

Vara, J., Lewandowska-Skarbek, M., Wang, Y.-G., Donadio, S., and Hutchinson, C. R. (1989) Cloning of genes governing the deoxysugar portion of the erythromycin biosynthesis pathway in saccharopolyspora erythraea (*Streptomyces erythreus*). *J. Bacteriol.* 171: 5872–5881.

Vijgenboom, E., Woudt, L. P., Heinstra, P. W. H., Rietveld, K., van Haarlem, J., van Wezel, G. P., Shochat, S., and Bosch, L. (1994) three tuf-like genes in the kirromycin producer *Streptomyces ramocissimus*. *Microbiology* 140: 983–998.

Ward, J. M., Janssen, G. R., Kieser, T., Bibb, M. J., Buttner, M. J., and Bibb, M. J. (1986) Construction and characterisation of a series of multi-copy promoter-probe plasmid vectors for Streptomyces using the aminoglycoside phosphotransferase gene from Tn5 as indicator. *Mol Gen Genet* 203: 468–475.

Yanish-Perron, Vieira, J., and Messing, J. (1985) Improved M13 phage cloning vectors and host strains: nucleotide sequences of the M13 mp18 and pUC19 vectors. *Gene* 33: 103 119.

SEQUENCE LISTING

```
<160> NUMBER OF SEQ ID NOS: 13

<210> SEQ ID NO 1
<211> LENGTH: 438
<212> TYPE: DNA
<213> ORGANISM: Streptomyces griseus

<400> SEQUENCE: 1
atgcgcgagt cggttcaagc agaggtcatg atgagcttcc tcgtctccga ggagctctcg      60
ttccgtattc cggtggagct ccgatacgag gtcggcgatc cgtatgccat ccggatgacg     120
ttccaccttc ccggcgatgc ccctgtgacc tgggcgttcg gccgcgagct gctgctggac     180
gggctcaaca gcccgagcgg cgacggcgat gtgcacatcg gcccgaccga gcccgagggc     240
ctcggagatg tccacatccg gctccaggtc ggcgcggacc gtgcgctgtt ccgggcgggg     300
acggcaccgc tggtggcgtt cctcgaccgg acggacaagc tcgtgccgct cggccaggag     360
cacacgctgg gtgacttcga cggcaacctg gaggacgcac tgggccgcat cctcgccgag     420
gagcagaacg ccggctga                                                    438

<210> SEQ ID NO 2
<211> LENGTH: 407
<212> TYPE: DNA
<213> ORGANISM: Streptomyces griseus
<220> FEATURE:
<221> NAME/KEY: CDS
<222> LOCATION: (1)..(405)

<400> SEQUENCE: 2 atg agc ttc ctc gtc tcc gag gag ctc tcg ttc cgt att ccg gtg gag        48
Met Ser Phe Leu Val Ser Glu Glu Leu Ser Phe Arg Ile Pro Val Glu
1               5                   10                  15 ctc cga tac gag gtc ggc gat ccg tat gcc atc cgg atg acg ttc cac        96
Leu Arg Tyr Glu Val Gly Asp Pro Tyr Ala Ile Arg Met Thr Phe His
            20                  25                  30 ctt ccc ggc gat gcc cct gtg acc tgg gcg ttc ggc cgc gag ctg ctg       144
Leu Pro Gly Asp Ala Pro Val Thr Trp Ala Phe Gly Arg Glu Leu Leu
        35                  40                  45 ctg gac ggg ctc aac agc ccg agc ggc gac ggc gat gtg cac atc ggc       192
Leu Asp Gly Leu Asn Ser Pro Ser Gly Asp Gly Asp Val His Ile Gly
    50                  55                  60
```

```
ccg acc gag ccc gag ggc ctc gga gat gtc cac atc cgg ctc cag gtc      240
Pro Thr Glu Pro Glu Gly Leu Gly Asp Val His Ile Arg Leu Gln Val
 65              70                  75                  80 ggc gcg gac cgt gcg ctg ttc cgg gcg ggg acg gca ccg ctg gtg gcg      288
Gly Ala Asp Arg Ala Leu Phe Arg Ala Gly Thr Ala Pro Leu Val Ala
                 85                  90                  95 ttc ctc gac cgg acg gac aag ctc gtg ccg ctc ggc cag gag cac acg      336
Phe Leu Asp Arg Thr Asp Lys Leu Val Pro Leu Gly Gln Glu His Thr
            100                 105                 110 ctg ggt gac ttc gac ggc aac ctg gag gac gca ctg ggc cgc atc ctc      384
Leu Gly Asp Phe Asp Gly Asn Leu Glu Asp Ala Leu Gly Arg Ile Leu
        115                 120                 125 gcc gag gag cag aac gcc ggc tg                                       407
Ala Glu Glu Gln Asn Ala Gly
    130                 135

<210> SEQ ID NO 3
<211> LENGTH: 135
<212> TYPE: PRT
<213> ORGANISM: Streptomyces griseus

<400> SEQUENCE: 3

Met Ser Phe Leu Val Ser Glu Glu Leu Ser Phe Arg Ile Pro Val Glu
 1               5                  10                  15

Leu Arg Tyr Glu Val Gly Asp Pro Tyr Ala Ile Arg Met Thr Phe His
            20                  25                  30

Leu Pro Gly Asp Ala Pro Val Thr Trp Ala Phe Gly Arg Glu Leu Leu
        35                  40                  45

Leu Asp Gly Leu Asn Ser Pro Ser Gly Asp Gly Asp Val His Ile Gly
    50                  55                  60

Pro Thr Glu Pro Glu Gly Leu Gly Asp Val His Ile Arg Leu Gln Val
 65              70                  75                  80

Gly Ala Asp Arg Ala Leu Phe Arg Ala Gly Thr Ala Pro Leu Val Ala
                 85                  90                  95

Phe Leu Asp Arg Thr Asp Lys Leu Val Pro Leu Gly Gln Glu His Thr
            100                 105                 110

Leu Gly Asp Phe Asp Gly Asn Leu Glu Asp Ala Leu Gly Arg Ile Leu
        115                 120                 125

Ala Glu Glu Gln Asn Ala Gly
    130                 135

<210> SEQ ID NO 4
<211> LENGTH: 407
<212> TYPE: DNA
<213> ORGANISM: Streptomyces albus G
<220> FEATURE:
<221> NAME/KEY: CDS
<222> LOCATION: (1)..(405)

<400> SEQUENCE: 4 atg agc ttc ctc gtc tcc gag gag ctc gcc ttc cgc atc ccg gtg gag       48
Met Ser Phe Leu Val Ser Glu Glu Leu Ala Phe Arg Ile Pro Val Glu
 1               5                  10                  15 ctg cgg tac gag acc gtc gat ccg tac gcg gtg cgg ctg acg ttc cac       96
Leu Arg Tyr Glu Thr Val Asp Pro Tyr Ala Val Arg Leu Thr Phe His
            20                  25                  30 ctc ccc gga gac gcc ccg gtc acc tgg gtc ttc ggg cgt gaa ctg ctg      144
Leu Pro Gly Asp Ala Pro Val Thr Trp Val Phe Gly Arg Glu Leu Leu
        35                  40                  45 gtc gag gga gtc ctg gac gcc gcg ggc gac ggc gac gtc cgg gtc tgc      192
```

```
Val Glu Gly Val Leu Asp Ala Ala Gly Asp Gly Asp Val Arg Val Cys
    50                  55                  60 ccg gtg ggg cag acg gcc acc agg gag gtg cac atc acc ctc cag gtc      240
Pro Val Gly Gln Thr Ala Thr Arg Glu Val His Ile Thr Leu Gln Val
65                  70                  75                  80 ggc tcc gag cag gcg ctc ttc cgc gtc ggc aag gcg ccg ctg ctc gcc      288
Gly Ser Glu Gln Ala Leu Phe Arg Val Gly Lys Ala Pro Leu Leu Ala
                85                  90                  95 ttc ctc gac cgc acc gac cag ggc ttg tcg ctc ggc agc gag cgg gca      336
Phe Leu Asp Arg Thr Asp Gln Gly Leu Ser Leu Gly Ser Glu Arg Ala
                100                 105                 110 cac gcc gac ttc gac agc cac ctc gac gac gct ctg aac cgc agc ctc      384
His Ala Asp Phe Asp Ser His Leu Asp Asp Ala Leu Asn Arg Ser Leu
            115                 120                 125 gcc gag gag cag agc gcc ggc tg                                       407
Ala Glu Glu Gln Ser Ala Gly
        130                 135

<210> SEQ ID NO 5
<211> LENGTH: 135
<212> TYPE: PRT
<213> ORGANISM: Streptomyces albus G

<400> SEQUENCE: 5

Met Ser Phe Leu Val Ser Glu Glu Leu Ala Phe Arg Ile Pro Val Glu
1               5                   10                  15

Leu Arg Tyr Glu Thr Val Asp Pro Tyr Ala Val Arg Leu Thr Phe His
            20                  25                  30

Leu Pro Gly Asp Ala Pro Val Thr Trp Val Phe Gly Arg Glu Leu Leu
        35                  40                  45

Val Glu Gly Val Leu Asp Ala Ala Gly Asp Gly Asp Val Arg Val Cys
    50                  55                  60

Pro Val Gly Gln Thr Ala Thr Arg Glu Val His Ile Thr Leu Gln Val
65                  70                  75                  80

Gly Ser Glu Gln Ala Leu Phe Arg Val Gly Lys Ala Pro Leu Leu Ala
                85                  90                  95

Phe Leu Asp Arg Thr Asp Gln Gly Leu Ser Leu Gly Ser Glu Arg Ala
                100                 105                 110

His Ala Asp Phe Asp Ser His Leu Asp Asp Ala Leu Asn Arg Ser Leu
            115                 120                 125

Ala Glu Glu Gln Ser Ala Gly
        130                 135

<210> SEQ ID NO 6
<211> LENGTH: 407
<212> TYPE: DNA
<213> ORGANISM: Streptomyces goldeniensis
<220> FEATURE:
<221> NAME/KEY: CDS
<222> LOCATION: (1)..(405)

<400> SEQUENCE: 6 atg agc ttc ctc gtc tcg gaa gaa ctc tcc ttc cgt att ccg gtg gag      48
Met Ser Phe Leu Val Ser Glu Glu Leu Ser Phe Arg Ile Pro Val Glu
1               5                   10                  15 ctg cgt tac gag acc tgt gat ccc tac gcc gtg cgg ctg acc ttt cat      96
Leu Arg Tyr Glu Thr Cys Asp Pro Tyr Ala Val Arg Leu Thr Phe His
            20                  25                  30 ctg ccc gga gat gcc ccg gtg acc tgg gcg ttc ggg cgg gag ttg ctc     144
Leu Pro Gly Asp Ala Pro Val Thr Trp Ala Phe Gly Arg Glu Leu Leu
```

```
atc gac gga ggt ccg cgg ccg tgc ggg gac ggg gac gtc cac atc gcg      192
Ile Asp Gly Gly Pro Arg Pro Cys Gly Asp Gly Asp Val His Ile Ala
         50                  55                  60 ccc gcc gac ccg gag acg ttc ggc gag gtc ctg atc cgc ctg cag gtg      240
Pro Ala Asp Pro Glu Thr Phe Gly Glu Val Leu Ile Arg Leu Gln Val
 65                  70                  75                  80 ggg agc gac cag gcg atg ttc cgg gtc ggc acg gcg ccg ctg gtg gcc      288
Gly Ser Asp Gln Ala Met Phe Arg Val Gly Thr Ala Pro Leu Val Ala
                 85                  90                  95 ttc ctg gac cgc acg gac aag atc gtg ccg ctg ggg cag gag cgt tcc      336
Phe Leu Asp Arg Thr Asp Lys Ile Val Pro Leu Gly Gln Glu Arg Ser
            100                 105                 110 ctc gcc gac ttc gac gcc ctg ctc gac gag gcg ctg gac cgc atc ctg      384
Leu Ala Asp Phe Asp Ala Leu Leu Asp Glu Ala Leu Asp Arg Ile Leu
            115                 120                 125 gcc gag gag cag aac gcc ggc tg                                       407
Ala Glu Glu Gln Asn Ala Gly
        130                 135

<210> SEQ ID NO 7
<211> LENGTH: 135
<212> TYPE: PRT
<213> ORGANISM: Streptomyces goldeniensis

<400> SEQUENCE: 7

Met Ser Phe Leu Val Ser Glu Glu Leu Ser Phe Arg Ile Pro Val Glu
  1               5                  10                  15

Leu Arg Tyr Glu Thr Cys Asp Pro Tyr Ala Val Arg Leu Thr Phe His
             20                  25                  30

Leu Pro Gly Asp Ala Pro Val Thr Trp Ala Phe Gly Arg Glu Leu Leu
         35                  40                  45

Ile Asp Gly Gly Pro Arg Pro Cys Gly Asp Gly Asp Val His Ile Ala
     50                  55                  60

Pro Ala Asp Pro Glu Thr Phe Gly Glu Val Leu Ile Arg Leu Gln Val
 65                  70                  75                  80

Gly Ser Asp Gln Ala Met Phe Arg Val Gly Thr Ala Pro Leu Val Ala
                 85                  90                  95

Phe Leu Asp Arg Thr Asp Lys Ile Val Pro Leu Gly Gln Glu Arg Ser
            100                 105                 110

Leu Ala Asp Phe Asp Ala Leu Leu Asp Glu Ala Leu Asp Arg Ile Leu
            115                 120                 125

Ala Glu Glu Gln Asn Ala Gly
        130                 135

<210> SEQ ID NO 8
<211> LENGTH: 407
<212> TYPE: DNA
<213> ORGANISM: Streptomyces netropsis
<220> FEATURE:
<221> NAME/KEY: CDS
<222> LOCATION: (1)..(405)

<400> SEQUENCE: 8 atg agc ttc ctc gtc tcc gag gag ctc tcc ttc aag atc cca gtc gaa       48
Met Ser Phe Leu Val Ser Glu Glu Leu Ser Phe Lys Ile Pro Val Glu
  1               5                  10                  15 ctg cga tac gag acc cgg gat ccc tac gcg gtg cgg atg acc ttc cac       96
Leu Arg Tyr Glu Thr Arg Asp Pro Tyr Ala Val Arg Met Thr Phe His
             20                  25                  30
```

| | | | | | | | | | | | | | | | | |
|---|---|---|---|---|---|---|---|---|---|---|---|---|---|---|---|---|
| ctc | ccc | gga | gac | gcg | cct | gtg | acc | tgg | gcg | ttc | ggc | cgg | gag | ctg | ctg | 144 |
| Leu | Pro | Gly | Asp | Ala | Pro | Val | Thr | Trp | Ala | Phe | Gly | Arg | Glu | Leu | Leu | |
| | | | | 35 | | | | 40 | | | | | 45 | | | |
| ctc | gac | ggg | atc | aac | cgc | ccg | agc | ggc | gac | ggc | gac | gtc | cac | atc | gcc | 192 |
| Leu | Asp | Gly | Ile | Asn | Arg | Pro | Ser | Gly | Asp | Gly | Asp | Val | His | Ile | Ala | |
| 50 | | | | | 55 | | | | | 60 | | | | | | |
| ccg | acc | gac | ccc | gag | ggc | ctg | tcg | gac | gtc | tcc | atc | cgg | ctc | cag | gtg | 240 |
| Pro | Thr | Asp | Pro | Glu | Gly | Leu | Ser | Asp | Val | Ser | Ile | Arg | Leu | Gln | Val | |
| 65 | | | | | 70 | | | | | 75 | | | | | 80 | |
| ggc | gcg | gac | cgc | gcc | ctc | ttc | cgt | gca | ggc | gcc | ccg | ctg | gtc | gcc | | 288 |
| Gly | Ala | Asp | Arg | Ala | Leu | Phe | Arg | Ala | Gly | Ala | Pro | Pro | Leu | Val | Ala | |
| | | | | 85 | | | | 90 | | | | | 95 | | | |
| ttc | ctc | gac | cgc | acg | gac | aag | tcg | gtg | ccg | ctc | ggt | cag | gaa | cag | act | 336 |
| Phe | Leu | Asp | Arg | Thr | Asp | Lys | Ser | Val | Pro | Leu | Gly | Gln | Glu | Gln | Thr | |
| | | | 100 | | | | | 105 | | | | | 110 | | | |
| ctg | ggt | gac | ttc | gag | gac | agc | ctg | gag | gcc | gcg | ctc | ggc | aag | atc | ctc | 384 |
| Leu | Gly | Asp | Phe | Glu | Asp | Ser | Leu | Glu | Ala | Ala | Leu | Gly | Lys | Ile | Leu | |
| | | | 115 | | | | | 120 | | | | | 125 | | | |
| gcc | gag | gag | cag | aac | gcc | ggc | tg | | | | | | | | | 407 |
| Ala | Glu | Glu | Gln | Asn | Ala | Gly | | | | | | | | | | |
| | 130 | | | | | 135 | | | | | | | | | | |

<210> SEQ ID NO 9
<211> LENGTH: 135
<212> TYPE: PRT
<213> ORGANISM: Streptomyces netropsis

<400> SEQUENCE: 9

Met Ser Phe Leu Val Ser Glu Glu Leu Ser Phe Lys Ile Pro Val Glu
1               5                   10                  15

Leu Arg Tyr Glu Thr Arg Asp Pro Tyr Ala Val Arg Met Thr Phe His
            20                  25                  30

Leu Pro Gly Asp Ala Pro Val Thr Trp Ala Phe Gly Arg Glu Leu Leu
        35                  40                  45

Leu Asp Gly Ile Asn Arg Pro Ser Gly Asp Gly Asp Val His Ile Ala
    50                  55                  60

Pro Thr Asp Pro Glu Gly Leu Ser Asp Val Ser Ile Arg Leu Gln Val
65                  70                  75                  80

Gly Ala Asp Arg Ala Leu Phe Arg Ala Gly Ala Pro Pro Leu Val Ala
                85                  90                  95

Phe Leu Asp Arg Thr Asp Lys Ser Val Pro Leu Gly Gln Glu Gln Thr
            100                 105                 110

Leu Gly Asp Phe Glu Asp Ser Leu Glu Ala Ala Leu Gly Lys Ile Leu
        115                 120                 125

Ala Glu Glu Gln Asn Ala Gly
    130                 135

<210> SEQ ID NO 10
<211> LENGTH: 34
<212> TYPE: DNA
<213> ORGANISM: Primer ssg1

<400> SEQUENCE: 10
ggcgaattcg aacagctacg tggcgaagtc gcca                                34

<210> SEQ ID NO 11
<211> LENGTH: 32
<212> TYPE: DNA
<213> ORGANISM: Primer ssg2

```
<400> SEQUENCE: 11
gtgggatccg tgctcgcggc gctggtcgtc tc                              32

<210> SEQ ID NO 12
<211> LENGTH: 32
<212> TYPE: DNA
<213> ORGANISM: Primer ssg3

<400> SEQUENCE: 12
gggaattcca tatgcgcgag tcggttcaag ca                              32

<210> SEQ ID NO 13
<211> LENGTH: 25
<212> TYPE: DNA
<213> ORGANISM: Primer ssg4

<400> SEQUENCE: 13
ccggtcagcc ggcgttctgc tcctc                                      25
```

What is claimed is:

1. A method for producing a recombinant *Streptomyces bacterium*, said method comprising:

transforming or transfecting a *Streptomyces bacterium* with an expressible polynucleotide encoding a heterologous SsgA that is not present in the *Streptomyces bacterium* in nature, the heterologous SsgA comprising at least one of SEQ ID NO: 3, SEQ ID NO: 5, SEQ ID NO: 7 and SEQ ID NO: 9, said *Streptomyces bacterium* lacking detectable endogenous SsgA during submerged culture.

2. The method according to claim 1, wherein said expressible polynucleotide is integrated into the genome of the *Streptomyces bacterium*.

3. The method according to claim 1, wherein said expressible polynucleotide is part of an episomal element.

4. The method according to claim 1, wherein expression of the expressible polynucleotide is inducible or repressible with a signal.

5. The method according to claim 1, wherein said *Streptomyces bacterium* produces a useful product.

6. The method according to claim 5 wherein said useful product is an antibiotic.

7. The method according to claim 5, wherein said useful product is a protein.

8. The method according to claim 7, wherein said protein is heterologous to said *Streptomyces bacterium*.

9. The method according to claim 7, wherein said protein is expressed from a vector encoding said protein present in said *Streptomyces bacterium*.

10. The method according to claim 9, wherein said protein is secreted by said *Streptomyces bacterium*.

11. The method according to claim 1, wherein the expressible polynucleotide comprise SEQ ID NO:1.

12. A method for producing a recombinant *Actinomycete bacterium*, said method comprising:

transforming an *Actinomycete bacterium* lacking a detectable endogenous SsgA with a nucleic acid encoding a heterologous SsgA comprising at least one of SEQ ID NO: 3, SEQ ID NO: 5, SEQ ID NO: 7 and SEQ ID NO: 9;

wherein the *Actinomycete bacterium* is selected from the group consisting of *Streptomyces clavuligerus* and *Streptomyces eryhraea*.

13. A method for producing a recombinant *Saccharopolyspora bacterium*, said method comprising transforming a *Saccharopolyspora bacterium* with an expressible polynucleotide encoding a heterologous SsgA comprising at least one of SEQ ID NO: 3, SEQ ID NO: 5, SEQ ID NO: 7 and SEQ ID NO: 9.

* * * * *

UNITED STATES PATENT AND TRADEMARK OFFICE
CERTIFICATE OF CORRECTION

PATENT NO. : 7,022,526 B2  
APPLICATION NO. : 09/749185  
DATED : April 4, 2006  
INVENTOR(S) : Gilles Philippus van Wezel, Barend Kraal and Rudolf Gijbertus M. Luiten It is certified that error appears in the above-identified patent and that said Letters Patent is hereby corrected as shown below:

In the specification:

| | | |
|---|---|---|
| COLUMN 5, | LINE 19, | change "ml" to --$ml^{-1}$-- |
| COLUMN 5, | LINE 63, | change "ermB" to --ermE-- |
| COLUMN 6, | LINE 11, | change "sagA" to --ssgA-- |
| COLUMN 7, | LINE 64, | change "saga" to --ssgA-- |
| COLUMN 7, | LINE 65, | change "streptamycetes" to --streptomycetes-- |
| COLUMN 7, | LINE 67, | change "*qoldeniensis*" to --*goldeniensis*-- |
| COLUMN 8, | LINE 35, | change "sagA" to --ssgA-- |
| COLUMN 9, | LINE 2, | change "saga" to --ssgA-- |
| COLUMN 9, | LINE 17, | change "GASL" to --GSA1-- |
| COLUMN 9, | LINE 26, | change "saga" to --ssgA-- |
| COLUMN 10, | LINE 15, | change "$P_{armk}$" to --$P_{ermE}$-- |
| COLUMN 11, | LINE 41, | change "*exythraea*" to --*erythraea*-- |
| COLUMN 12, | LINE 29, | change "is that" to --that-- |

Signed and Sealed this

Sixteenth Day of December, 2008

JON W. DUDAS  
*Director of the United States Patent and Trademark Office*